US00PP28388P3

(12) United States Plant Patent
Chauhan et al.

(10) Patent No.: US PP28,388 P3
(45) Date of Patent: Sep. 12, 2017

(54) VETIVER PLANT NAMED 'CIMAP-KHUSINOLIKA'

(50) Latin Name: ***Vetiveria* (syn. *Chrysopogon*) *zizanioides***
Varietal Denomination: CIMAP-KHUSINOLIKA

(71) Applicant: Council of Scientific and Industrial Research, New Delhi (IN)

(72) Inventors: Harmesh Singh Chauhan, Lucknow (IN); Hemendra Pratap Singh, Lucknow (IN); Chandan Singh Chanotiya, Lucknow (IN); Ajit Kumar Shasany, Lucknow (IN); Umesh Chandra Lavania, Lucknow (IN); Virendra Kumar Singh Tomar, Lucknow (IN); Alok Kalra, Lucknow (IN); Ashok Kumar Singh, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 36 days.

(21) Appl. No.: 14/545,762

(22) Filed: Jun. 15, 2015

(65) Prior Publication Data

US 2016/0366805 P1 Dec. 15, 2016

(51) Int. Cl.
*A01H 5/12* (2006.01)

(52) U.S. Cl.
USPC ..... Plt./384

(58) Field of Classification Search
USPC ..... Plt./384
See application file for complete search history.

(56) References Cited

U.S. PATENT DOCUMENTS

PP26,474 P3 3/2016 Lavania et al.

OTHER PUBLICATIONS

"Vetiver Grass: A Thin Green Line Against Erosion", Panel on Vetiver, Board on Science and Technology for International Development, National Research Council, (1993), 1-186.
Guenther, E., "Oil of Vetiver", *The Essential Oils*, vol. 4, Robert E. Krieger Publishing Co., Inc., Huntington, New York, NY, (1972), 156-180.
Kelly, R. B., et al., "A Total Synthesis of Cadin-4, 10(15)-dien-3α-ol: Structure of Khusinol", *Canadian Journal of Chemistry*, 50, (1972), 3272-3275.
Kirici, et al., "To Study of Essential Oil and Agricultural Properties of Vetiver (*Vetiveria zizanioides*) in the Southeastern of Mediterranean", *Advances in Environmental Biology*, 5(2), (2011), 447-451.
Lai, R. K., "Genetic variability and association analysis for yield and yield components in indigenous and exotic collections of vetiver (*Vetiveria zizanioides* (L.) Nash)", *Journal of Spices and Aromatic Crops* 9(2), (2000), 133-136.
Lavania, U. C., et al., "Vetiver system ecotechnology for water quality improvement and environment enhancement",*Current Science*, 86(1), (2004), 11-14.
Martinez, Julian, et al., "Valorization of Brazilian Vetiver (*Vetiveria zizanioides* (L.) Nash ex Small) Oil", *J. Agric. Food Chem.*, 52, (2004), 6578-6584.
Ogilvie, K. K., et al., "Synthesis of 8,3'-Thioanhydroguanosine", *Can. J. Chem.*, vol. 50, downloaded from www.nrcresearchpress.com by 117.197.17.73 on Dec. 7, 2015, (1972), 3276-3280.
Trivedi, G. K., et al., "Terpenoids-LXXVI: Transformation products from $BF_3$-catalysed reaction of khusinol"; *Tetrahedron*, 22(5), (1966), 1641-1649.
"Vetiver Grass Training Manual", The Office of the Royal Development Project Boards (ORDPB) Thailand, (Jan. 2001), 137 pgs.
Lavania, U. C., "Vetiver in India: Historical Perspective and Prospective for Development of Specific Genotypes for Environmental or Industrial Application", Updated: In: Proc. First Indian National Vetiver Workshop, Vector System for Environmental Protection and Natural Disaster Management, (Cochin, India Feb. 21-23, 1988), Truong P., Editor, (1988), 40-47.
Rao, A. A., et al., "Terpenoids—XXXVI : The structure of khusinol a new sesquiterpene alcohol from vetiver oil", Tetrahedron, vol. 19, Issue 1, 1963, pp. 233-239, (May 22, 1962), 233-239.

*Primary Examiner* — Susan McCormick Ewoldt
(74) *Attorney, Agent, or Firm* — Schwegman Lundberg & Woessner, P.A.

(57) ABSTRACT

The present invention relates to the development of a novel, morphologically and genetically distinct khusinol rich essential oil producing clone of vetiver [*Vetiveria zizaniodes* (L.) Nash. syn. *Chrysopogon zizanioides* (L.) Roberty; family Poacaeae} named 'CIMAP-Khusinolika'. The plant of this clone is characterized by spreading type clump canopy in the initial stage, white feathery stigma and capable of producing >1% (v/w) essential oil containing 45-50% Khusinol (v/v) obtained after hydro-distillation from fresh roots harvested from 6 month old plantations. This clone has unique ISSR profiles that serve as DNA-fingerprints. The clone was obtained through recurrent selection in polycrossed population generated from the bulk of wild collection, and can be propagated through vegetative slips (3 to 6 month old stem with few roots) for commercial plantation as a short duration crop.

2 Drawing Sheets

VETIVER PLANT NAMED 'CIMAP-KHUSINOLIKA'

Figure 1:
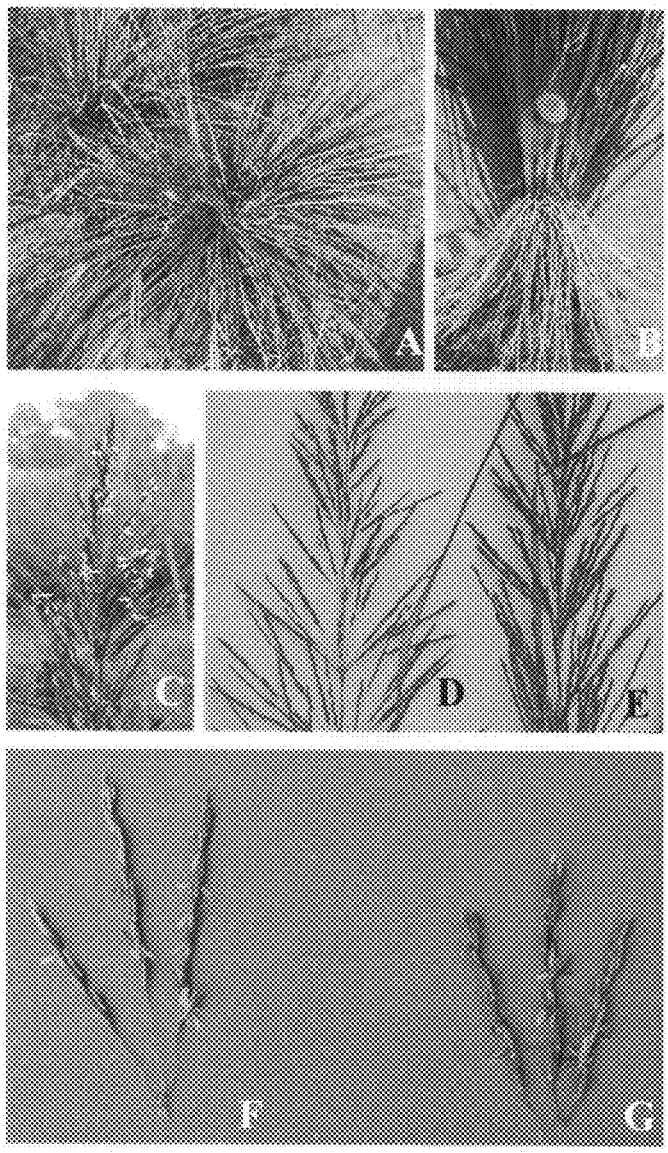

Latin name of the genus and species claimed: *Vetiveria* (syn. *Chrysopogon*) Species: *zizanioides*.

Variety denomination: 'CIMAP-KHUSINOLIKA'.

FIELD OF THE INVENTION

The present invention is related to the development of a novel, distinct, khusinol rich, short duration, spread clump behavior plant type (clone) of vetiver (*Chrysopogon zizanioides*) obtained through recurrent selection in polycrossed population generated from the bulk of wild collections, Vetiver plant named 'CIMAP-KHUSINOLIKA' with the Latin name *Chrysopogon zizaniodes*, and the varietal denomination of 'CIMAP-KHUSINOLIKA'. The mass propagation of this clone is through vegetative multiplication using slips (3 to 6 month old stem with few roots), and hence this plant is genetically uniform and stable. This has unique spread clump growth behavior, not observed in other varieties and genotypes. The clone holds commercial advantage since the plant roots of desirable quality can be harvested after 6 months that contain high essential oil content (1% v/w), rich in Khusinol (45% v/v), not reported in any other variety and genotype. That is, a new and distinct variety of diploid (2n=20) plant named 'CIMAP-KHUSINOLIKA' of Vetiver as illustrated and described herein is provided (*Vetiveria zizaniodes* (L.) Nash. syn. *Chrysopogon zizanioides* (L.) Roberty). The plant is capable of producing >1% (v/w) essential oil from fresh roots harvested after 6 months of plantation higher than any other commercial genotype harvested after six months duration, containing more than >45% (v/v) Khusinol in the essential obtained from fresh roots of six month old plants, compared to all other varieties that have only 10-20% Khusinol content in their essential oil, a short crop-gestation of six months for economic harvest, compared to standard 18 months required for the other existing varieties, prostrate-spreading type of initial growth habit at 2-3 month stage and then growing erect, flowers in August, i.e. a delay in flowering by approx. two months compared to other varieties, lax inflorescence with smaller floret/seed size (smaller by approx 15% compared to standard), smaller feathery white stigman, and producing 65 g roots/plant from 6 month old plant grown under Lucknow conditions during July-December cropping season, having roots with a diameter 1.7 mm at the base.

BACKGROUND OF THE INVENTION AND DESCRIPTION OF PRIOR ART

Khus or Vetiver (*Vetiveria zizaniodes* (L.) Nash., syn. *Chrysopogon zizaniodes* (L.) Roberty; family Poacaeae), is a perennial, wildly growing aromatic plant occurring all across India in variable agro-climatic conditions. India is considered to be the center of origin of vetiver (Lavania UC (2008): Vetiver in India: historical perspective and prospective for development of specific genotypes for environmental or industrial application. In, Truong P (ed.) Proc First Indian National Vetiver Workshop: Vetiver system for environmental protection and natural disaster management, Cochin, India 21-23 Feb. 1988, pages 40-47. As such, a higher order of genetic diversity with respect to ecological/geographic adaptation, morphometric traits, reproductive behaviour and essential oil concentration and composition is found in the Indian subcontinent, followed by Indonesia (Lal RK (2000) Genetic variability and association analysis for yield and yield components in indigenous and exotic collections of vetiver (*Vetiveria zizanioides* (L.) Nash). *Jour. Spices Aromatic Crops* 9: 133-136.).

Roots of vetiver are the source of world famous "Khus oil" which has considerable value in essential oil industry. Indians were the first to recognize vetiver for its aromatic and medicinal uses, followed by its other cottage and environmental uses in India and elsewhere (Lavania UC (2003) *Vetiver root oil, and its utilization. Pacific Rim Vetiver Network Technical Bulletin*, No. 2003/1, 12 pages, Office of the Royal Development Projects Board, Bangkok, Thailand, Lavania UC, Lavania S and Vimala Y. 2004. Vetiver system ecotechnology for water quality improvement and environmental enhancement. Current Science 86:11-14, Lavania UC (2008). The total world production of khus oil is estimated to be 250-300 tonnes per year. In India, about 20-25 tonnes oil is produced annually, which is much below to meet even the indigenous demand of the oil for perfume, essence, attar and soap industries.

Two distinct morphological complexes of vetiver are found to inhabit spatially separated geographic regions in India: one in the north along the Indo-gangetic plains and adjoining areas mainly in the states of Rajasthan, Madhya Pradesh, Uttar Pradesh and Bihar, and the other in the south along the east and west coasts of Indian peninsula in the states of Andhra Pradesh, Karnataka, Tamilnadu and Kerala. The two races are distinctly different. The north Indian wild types represented by "Bharatpur type" are profuse flowering high seed-setting having narrow leaves with vigorous roots producing low concentration superior quality laevorotatory root oil (ruh-khus or khus oil) and the south Indian "cultivated type" that are late and low flowering with high pollen sterility and non seed-setting with wider leaves producing low quality dextrorotatory root oil (vetiver oil) resembling Java vetiver (see, Lavania 2008). Depending upon the oil quality and free vetiverols, there could be a price difference of four fold between laevorotatory and dextrorotatory oils. The former mainly available in north Indian vetiver is considered to be superior quality (Lavania 2003).

Systematic cultivation of vetiver has been in practice in south India, mainly in Kerala (Thiruvambadi, Neyatunkara), Andhra Pradesh (East Godavari and Kurnool), Tamilnadu (Mettupalayam, Nilgiri and Coimbatore) and in small areas of Karnataka state. However, the Khus cultivation for profitability has been driven by increasing demand of its essential oil. As such, cultivation of vetiver has also been taken up in the Indian states of Uttar Preadesh and Bihar. However, its long duration (18 months) and poor root yields, variable oil content and quality and Khusinol (a desirable oxygenated sesquiterpine likened to Khusimol for its vetiverol characteristics) content just up to 10%, have hindered its acceptance among the farmers and perfume industry.

Extensive breeding efforts have been undertaken at various research centre in India to develop/identify suitable clones to produce homogenous population and uniform quality for its essential oil under vetiver cultivation (for details see Lavania 2008 for an overview), but the problem of long gestation period for crop under cultivation and quality of root-essential oil has long bothered the scientists.

The present invention i.e. 'CIMAP-KHUSINOLIKA', overcomes this problem to a large extent by reducing the crop gestation period just to six months, and at the same time realizing desired quality of essential oil rich in Khusinol. This clone could yield more than 1% essential oil concentration containing 45-50% Khusinol just after 6 months of planting. As a super-short duration clone, this plant type provides opportunities to suitably accommodate vetiver cultivation into existing cropping systems. It is worth emphasizing that in literature, the highest Khusinol in *Chrysopogon zizanoides* is reported to be 19.15% (Kirici S, Inan M, Turk M and Giray E. S. 2011. To Study of Essential Oil and Agricultural Properties of Vetiver (*Vetiveria Zizanioides*) in the Southeastern of Mediterranean. *Advances in Environmental Biology* 5: 447-451.). But this clone 'CIMAP-KHUSINOLIKA' is distinct and unique from all the available clones, since it is endowed with highest amount of sesquiterpene "khusinol", which is reported for the first time.

Khusinol is a sesquiterpene alcohol (with molecular weight 220), one among the group of 20 vetiverol sesquiterpene, found only in the essential oil of *Vetiveria zizanoides* contributes to pleasant aroma of vetiver oil along with khusimol and zizanol. Isolation of this sesquiterpenoid from a complex blend of vetiver essential oil is difficult. This is a cadinane-type compound (which usually used as wood protective probably due to some repellant properties) used as a starting material for the synthesis of compounds like khusinodiol. Additionally other compounds namely (+)-α-cadinol and iso-khusinol are also synthesized by using khusinol (Trivedi G K, Wagh A D, Paknikar S K, Chakravarthi K K, Bhatacharya S C, Terpenoids—LXXVI: Transformation products from $BF_3$-catalysed reaction of khusinol. *Tetrahedron,* 1966, 22(5), 1641-1649). Hence high khusinol is desirable in the essential oil of vetiver.

OBJECTS OF THE INVENTION

Primary objective of this invention was to develop a novel, distinct, short duration plant of vetiver which could be harvested in 5-6 months.

Another objective of this invention was to generate a plant with sufficient oil yield at par or more with other varieties (at least 1.0% or more).

In yet another objective of the invention was to have a genotype yielding root essential oil having higher amount of Khusinol (45 to 55%) i.e. higher over any other available variety and genotype.

BRIEF DESCRIPTION OF THE ACCOMPANYING DRAWINGS

FIG. 1. Morphometric features: A. Plants of the clone 'CIMAP-Khusinolika' showing spreading canopy, B. Plant showing roots after six months, C. Inflorescence bearing flowers with white feathery stigma, D-E. Relative view of Spike features of the clone 'CIMAP-Khusinolika' i.e. D, compared with the standard type E (note lax nature in the D). F-G. Close-up of the Spikelets of the developed clone and the standard type: F. developed clone showing smaller flowers and white feathery stigma, compared to relatively larger flowers and purple colored stigma in the standard type.

Figure 2:
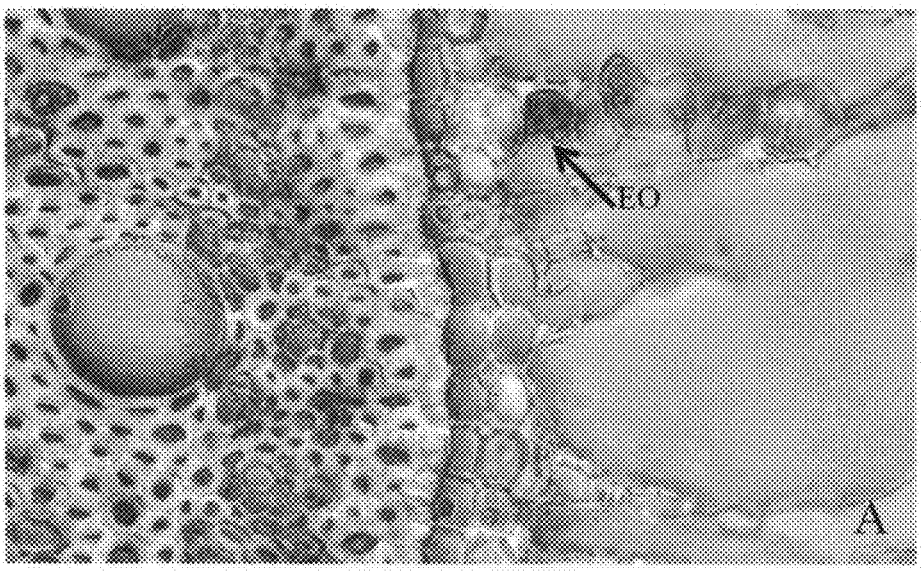
Figure 2:
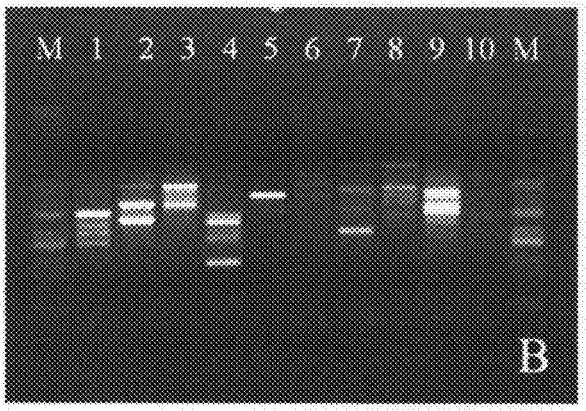
Figure 2:
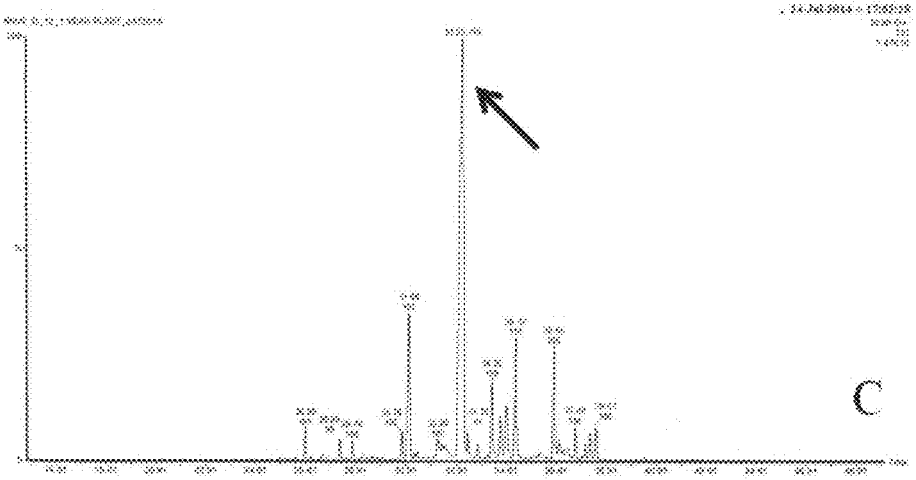

FIG. 2. Marker features of the developed clone: A. Root transverse section showing essential oil secretatory cells (EO), B. ISSR DNA finger prints, C. Gas Liquid Chromatograph of the essential oil obtained from the developed clone; the khusinol peak is arrow marked.

DETAILED DESCRIPTION OF THE INVENTION

Breeding History

Looking into the commercial importance of the vetiver oil obtainable from the roots of vetiver, extensive efforts have been made in India to develop improved varieties and clones in this essential oil crop (for an overview—see Lavania 2008). However, none led to the realization of a short duration plant type that could produce essential oil of superior quality. The development of the present clone fills this gap.

Method of Development of the Plant Clone 'CIMAP-KHUSINOLIKA'

India is the centre of diversity of vetiver. Plant grows wild throughout India, more particularly in peninsular India and plains of central and northern India. In the north Indian state of Uttar Pradesh its occurrence is quite profuse and huge amount of variation is noticeable in the wild populations. Therefore, an extensive population improvement programme was started to identify a genotype that could be suitable for cultivation under short duration fitting in cropping systems for production of its essential oil.

The clone 'CIMAP-KHUSINOLIKA' initially identified as strain "G-12" in the breeding population is a descendant from population improvement programme started in the cropping season of the year 2005-06 from bulk seeds of open-pollinated wild populations collected from Lucknow, Sitapur, Barabanki, Sultanpur, Raibareli, Fatehpur, Hardoi, Unnao and Kanpur of the state of Uttar Pradesh, India. For this breeding programme, a nursery was raised and 4000 plants were evaluated for high growth rate of root, essential oil content. In the year 2006-07, 200 best performing clones were evaluated in progeny row and after selection 10 elite clones were polycrossed (Open-pollinated elite lines were allowed to inter-mate each other in isolated polycrossing block). This bulked polycrossed seeds provided the base population for second cycle of recurrent selection and 100 best performing clones (oil content >1.00%) were selected. Out of these 40 top best performing clones were evaluated during year 2009-10 as IET (Table 1).

TABLE 1

Performance of 40 elite clones, during 2009-10 for oil content and root yield/plant in Initial Evaluation Trial (IET) after 18 months of plantation

| Accession No/strain | Oil content (%) | Root yield g/plant |
|---|---|---|
| G-1 | 1.77 | 59.28 |
| G-2 | 1.47 | 52.61 |
| G-3 | 2.08 | 40.17 |
| G-4 | 1.86 | 39.69 |
| G-5 | 1.84 | 46.83 |
| G-6 | 1.46 | 56.91 |
| G-7 | 1.95 | 45.81 |
| G-8 | 1.82 | 52.25 |
| G-9 | 2.14 | 42.57 |
| G-10 | 2.20 | 60.93 |
| G-11 | 1.85 | 55.30 |
| G-12 | 2.27 | 65.09 |
| G-13 | 2.12 | 42.81 |
| G-14 | 1.97 | 51.10 |
| **Ac no** | **Oil content (%)** | **Root yield g/plant** |
| G15 | 2.10 | 67.83 |
| G-16 | 1.46 | 40.90 |
| G-17 | 1.91 | 45.30 |
| G-18 | 2.16 | 46.34 |
| G-19 | 2.10 | 57.38 |

TABLE 1-continued

Performance of 40 elite clones, during 2009-10 for oil content and root yield/plant in Initial Evaluation Trial (IET) after 18 months of plantation

| | | |
|---|---|---|
| G-20 | 1.85 | 49.53 |
| G-21 | 1.74 | 48.87 |
| G-22 | 3.04 | 46.76 |
| G-23 | 1.94 | 43.29 |
| G-24 | 3.14 | 55.74 |
| G-25 | 1.60 | 44.11 |
| G-26 | 1.29 | 41.50 |
| G-27 | 2.76 | 54.42 |
| G-28 | 2.00 | 38.79 |
| G-29 | 2.06 | 53.98 |
| G-30 | 1.67 | 36.32 |
| G-31 | 1.99 | 46.04 |
| G-32 | 1.75 | 57.42 |
| G-33 | 1.31 | 48.19 |
| G-34 | 1.67 | 81.34 |
| G-35 | 1.93 | 51.82 |
| G-36 | 1.55 | 52.00 |
| G-37 | 1.61 | 48.20 |
| G-38 | 1.65 | 50.00 |
| G-39 | 1.50 | 46.50 |
| G-40 | 1.60 | 48.00 |
| SD | 0.394 | 8.747 |
| CV | 20.60 | 17.39 |

The selection was further narrowed down to 30 best clones and evaluated under multi location trials at eight different agro-climatic locations in year 2011-12 with five checks viz. 'KS-1', 'Kesary', 'Gulabi', 'Dharni' and 'CIM-Vridhi'. The Clones 15 and 22 based on the results of multi-location trials were released for commercial cultivation under Indian conditions. Further, 5 selections namely, G3, G12, G15, G16 and G21 on the basis of their growth behavior with distinct morphology+4 Checks namely KS-1, Dharini, Kesari and Gulabi) were again evaluated during rainy/monsoon season (July) of year 2013 for exploring the possibility of optimal oil yield under shortest duration and the observation on fresh root yield/plant and oil content had been recorded during December 2013 and the results are presented in table.2.

TABLE 2

Performance of 5 elite lines + 4 checks of vetiver in respect to fresh root and shoot weight (g)/plant and oil content (%) in PST after 06 months of plantation

| Strain | Fresh root weight g/plant | Fresh shoot weight g/plant | Root:Shoot | Oil content (%) |
|---|---|---|---|---|
| G3 | 70 | 543 | 0.1289 | 0.86 |
| G12 | 65 | 440 | 0.1478 | 1.08 |
| G15 | 74 | 699 | 0.1059 | 0.95 |
| G16 | 75 | 1000 | 0.0750 | 1.06 |
| G21 | 68 | 566 | 0.1201 | 0.88 |
| KS-1 | 76 | 1340 | 0.0567 | 0.79 |
| Dharini | 70 | 1150 | 0.0609 | 1.00 |
| Kesari | 100 | 1280 | 0.0781 | 0.80 |
| Gulabi | 81 | 1480 | 0.0547 | 0.98 |
| MEAN | 75.44 | | | 0.93 |
| SE± | 3.457 | | | 0.0356 |
| SD | 9.830 | | | 0.400 |
| Variance | 96.647 | | | 0.160 |

Of these selections, G12 was observed to be having highest Root: Shoot ratio (0.1478) and oil content (1.08% v/w). Another uniqueness of this plant was that the essential oil contains >45% Khusinol.

BOTANICAL DESCRIPTION AND CHARACTERIZATION

The new and distinct clone of *Chrysopogon zizanioides* 'CIMAP-Khusinolika' is suitable for cultivation as a short duration crop for its essential oil rich in khusinol. The latter has value in perfumery as such as well as a potential substitute/alternative to khusimol. The said clone is developed through recurrent selection in polycrossed progenies and possesses the following combination of characters:

Uniformity and stability: The instant plant type is a clone, tested for growth behavior, essential oil yield and essential oil quality that show its uniformity and stability examined over vegetative multiplication cycles. Sufficient quantity of planting material could be easily generated by asexual propagation through slips.

Flowering behavior: This clone is late flowering and low seed setter. Tested on annual growth cycle under Lucknow conditions it flowers in the months of August-September, compared to others that start flowering from April onward.

Growth behavior: In its initial growth stage at 2-3 months, the plant shows prostrate-spreading type of plant canopy. Under Lucknow conditions, a six month old plant planted at plant to row distance of 60×60 cms in the month of July and harvested at the end of December gives an average root yield of 65 g/plant. However, the flowering occurs only in the second year after initial planting.

Essential oil productivity: The fresh roots harvested from six month old plant on hydro-distillation for 18 hours yield 1% essential oil that contains 45-50% khusinol v/v.

Essential oil quality: Capillary GC-FID and GC/MS of the essential oil obtained from roots harvested after 6 months of planting and tested over two crops show presence of approx. 88% oxygenated sesquiterpenes; out of which Khusinol contributes 45-50%.

Morphological characterization:

*Genus.*—*Vetiveria* (syn. *Chrysopogon*).

*Species.*—*Zizanioides.*

*Family.*—Poaceae.

*Common name.*—Vetiver, Khus (in Hindi in India).

*Cultivar name.*—CIMAP-Khusinolika. It is a fast growing diploid (2n=20), late and low flowering clone, with spreading plant canopy initially, smaller stomata, lax inflorescence, smaller spikelets and white feathery stigma, capable of producing >1% essential oil rich in Khusinol (>45%) obtained from fresh roots after six months of plantation.

Morphometric description of the clone 'CIMAP-Khusinolika': Color determination is in accordance with The 2007 The Royal Horticultural Society Colour Chart, Royal Horticultural Society, London England.

General morphology: Spreading type above-ground canopy with tufted roots, late and low flowering; delay in flowering by over 45-60 days compared to other north Indian genotypes, and lax inflorescence with white feathery stigma Flowering occurs in the second year after initial planting.

*Plant height.*—1.0 to 1.7 m.

*Plant canopy.*—Spread, diameter 70 to 80 cms.

*Growth habit.*—Spreading plant type initially nearly prostrate but becomes erect at later stage, flowering is initiated in August (FIG. 1).

*Branching.*—Tillers.

*Culms.*—Compressed in early stages cylindrical in later stages, well defined nodes and internodes.

*Number of tillers.*—25 to 42 after six months (cf. 30-45 in standard check).

*Number of nodes in tillers.*—4 to 7.

*Average culm length.*—2.25 m (cf. 2.45 m in standard check).

*Leaf margin.*—Serrate, dorsal surface rough, ventral glabrous and rough along the edges.

*Leaf length.*—1.0 m to 1.5 m.

*Leaf width.*—8 mm to 10 mm.

*Lamina colour.*—RHS Green group (137-B).

*Leaf sheath colour.*—RHS Yellow green group (144-B).

*Tip.*—Acute.

*Stomata.*—Stomatal Index 19.5; size of stomatal complex and stomatal guard cell 498 $\mu m^2$ and 72.5 $\mu m^2$ respectively (compared to 870 $\mu m^2$ and 115 $\mu m^2$ in standard check).

*Inflorescence.*—Panicle (FIG. 2). Length of the flowering shoot, length of panicle bearing peduncle, length of spike bearing part of peduncle, number of spike bearing nodes in a peduncle, number of spikes per node, number of florets (diad) per spike rachilla (diad i.e. a pair of sessile and pedicellate spikelet), respectively are 235 cms, 85 cms, 40 cms, 13, 11, 13 compared to standard check respectively 245, 90, 38, 09, 17, 9.

*Inflorescence colour (RHS 5th Edition, London,* 2007).—Color of peduncle axis — RHS color — yellow group 144C (cf. standard check Grey Red group 182 B ), Color of Lemma — RHS color 53 B, Stigma feathery with RHS color — White group 155B (cf. standard check that has RHS-Grey purple group 183). Flower; Spikelets borne in pair of sessile (hermaphrodite) and pedicilled (staminate) having Glume (enclosing flower) length of 3.1 mm and 2.9 mm respectively, compared to 3.6 mm and 3.1 mm in the standard control.

*Stigma.*—Feathery with RHS color — White group 155B — this is a specific marker trait (cf. Grey purple group 183 in standard control and also common in other varieties).

*Flowering.*—Late flowering (in August under Lucknow conditions) compared to standard flowering in May and June.

*Seed.*—Oblong and oblique at the top.

*Root.*—Diameter near the root base 1.7 mm (compared 2.0+mm in others), colour pale whitish, average root length 15-20 cms.

*Essential oil content.*—Medium (1.0%) in freshly harvested roots having moisture content 45%.

*Physicochemical parameter of essential oil.*—

*Odor.*—Woody/earthy note.

*Colour.*—Light yellow in appearance.

*Refractive index* $n_D^{20}$.—1.5193-1.5209.

*Optical rotation* $[\alpha]$.—−68.680° at 23.8° C. temperature.

Chemical composition: Capillary GC-FID and GC/MS analysis of the essential oil obtained from roots harvested after 6 months of planting showed oxygenated sesquiterpenes (approx. 88%); out of which khusinol contribute approx. 47%.

*Khusinol content.*—45-50%.

*Fresh root yield.*—18-20 q/ha (At an average age of 6 months).

*Oil yield.*—18-20 kg/ha.

Distinguishing features and advantages of the clone 'CIMAP-KHUSINOLIKA'; Compared to all other varieties of vetiver, the said clone 'CIMAP-KHUSINOLIKA' is distinct in respect of combination of characters like: prostrate-spreading type growth habit at 2-3 months growth stage, lax inflorescence, smaller floret and seed size, white stigma, characteristic ISSR-DNA fingerprints. The clone offers the following distinct advantages over other existing clones/varieties of vetiver: This clone is suitable for commercial cultivation as short-duration crop that can give economic harvests just after six months of plantation, and can be suitably adjusted in an existing cropping system either as a sole or mixed crop The fresh roots harvested from six month old crop can yield essential oil concentration of >1% (v/w) after 16 hrs of hydrodistillation at 60° C., The essential oil obtained as above contains >45% (v/v) Khusinol content having high value in perfumery.

Distinctiveness of the plant through IISR fingerprints: DNA Fingerprints of clone 'CIM-Khusinolika' based on ISSR markers FIG. 2

SEQUENCE LISTING OF ISSR MARKERS USED

```
ISSR PRIMER UBC 807
                    SEQUENCE ID NO. 1
AGAGAGAGAG AGAGAGT

ISSR PRIMER UBC 810
                    SEQUENCE ID NO. 2
GAGAGAGAGA GAGAGAT

ISSR PRIMER UBC 811
                    SEQUENCE ID NO. 3
GAGAGAGAGA GAGAGAC

ISSR PRIMER UBC 812
                    SEQUENCE ID NO. 4
GAGAGAGAGA GAGAGAA

ISSR PRIMER UBC 814
                    SEQUENCE ID NO. 5
CTCTCTCTCT CTCTCTA

ISSR PRIMER UBC 818
                    SEQUENCE ID NO. 6
CACACACACA CACACAG

ISSR PRIMER UBC 823
                    SEQUENCE ID NO. 7
TCTCTCTCTCTCTCTCC

ISSR PRIMER UBC 825
                    SEQUENCE ID NO. 8
ACACACACAC ACACACT

ISSR PRIMER UBC 826
                    SEQUENCE ID NO. 9
ACACACACAC ACACACC

ISSR PRIMER UBC 828
                    SEQUENCE ID NO. 10
TGTGTGTGTG TGTGTGA
```

GENERAL REFERENCES

Guenther E (1972) The Essential Oils, vol 4. Rober E Krieger Publishing Co. Inc., Huntington, N.Y. Pp. 156-180.

Kelly R B and Eber J (1972) A total synthesis of Cadin-4, 10(15)-diden-3a-ol: Structure of Khusinol. Can. J. Chem 50:3272-3275.

Kirici S, Ivan M, Turk M and Giray E S. 2011. To Study of Essential Oil and Agricultural Properties of Vetiver (*Vetiv-*

*eria Zizanioides*) in the Southeastern of Mediterranean. *Advances in Environmental Biology* 5: 447-451

Lal R K (2000) Genetic variability and association analysis for yield and yield components in indigenous and exotic collections of vetiver (*Vetiveria zizanioides* (L.) Nash). Jour. Spices Aromatic Crops 9: 133-136.

Lavania U C (2003) Vetiver root oil, and its utilization. Pacific Rim Vetiver Network Technical Bulletin, No. 2003/1, 12 pages, Office of the Royal Development Projects Board, Bangkok, Thailand.

Lavania U C, Lavania S and Vimala Y. 2004. Vetiver system ecotechnology for water quality improvement and environmental enhancement. Current Science 86:11-14.

Lavania U C (2008): Vetiver in India: historical perspective and prospective for development of specific genotypes for environmental or industrial application. In, Truong P (ed.) Proc First Indian National Vetiver Workshop: Vetiver system for environmental protection and natural disaster management, Cochin, India 21-23 Feb. 1988, pages 40-47. http://www.vetiver.org/TVN_INDIA_1stWORKSHOP_PROCEEDINGS/Chapter%201-4.pdf Martinez J, Rosa-Paulo T V, Menut C, Leydet A, Brat P, Pallet D, Meireles M A A (2004) Valorization of Brazilian vetiver (*Vetiveria zizanioides* (L.) Nash ex Small) oil. Jour Agric and Food Chemistry 52:6578-6584.

Mannual: Factual tips about Vetiver grass. ISBN 974-7772-49-3. Office of the Royal Development Projects Board, Bangkok, Thailand, pp. 103.

National Research Council (1993) Vetiver grass: a thin green line against erosion. National Academy Press, Washington, D.C., pp.169.

Trivedi G K, Wagh A D, Paknikar S K, Chakravarthi K K, Bhatacharya S C, Terpenoids—LXXVI: Transformation products from $BF_3$-catalysed reaction of khusinol. *Tetrahedron,* 1966, 22(5), 1641-1649.

SEQUENCE LISTING

```
<160> NUMBER OF SEQ ID NOS: 10

<210> SEQ ID NO 1
<211> LENGTH: 17
<212> TYPE: DNA
<213> ORGANISM: Artificial Sequence
<220> FEATURE:
<223> OTHER INFORMATION: A synthetic ISSR PRIMER UBC 807

<400> SEQUENCE: 1

agagagagag agagagt                                                  17


<210> SEQ ID NO 2
<211> LENGTH: 17
<212> TYPE: DNA
<213> ORGANISM: Artificial Sequence
<220> FEATURE:
<223> OTHER INFORMATION: A synthetic ISSR PRIMER UBC 810

<400> SEQUENCE: 2

gagagagaga gagagat                                                  17


<210> SEQ ID NO 3
<211> LENGTH: 17
<212> TYPE: DNA
<213> ORGANISM: Artificial Sequence
<220> FEATURE:
<223> OTHER INFORMATION: A synthetic ISSR PRIMER UBC 811

<400> SEQUENCE: 3

gagagagaga gagagac                                                  17


<210> SEQ ID NO 4
<211> LENGTH: 17
<212> TYPE: DNA
<213> ORGANISM: Artificial Sequence
<220> FEATURE:
<223> OTHER INFORMATION: A synthetic ISSR PRIMER UBC 812

<400> SEQUENCE: 4

gagagagaga gagagaa                                                  17


<210> SEQ ID NO 5
<211> LENGTH: 17
<212> TYPE: DNA
<213> ORGANISM: Artificial Sequence
<220> FEATURE:
```

-continued

<223> OTHER INFORMATION: A synthetic ISSR PRIMER UBC 814

<400> SEQUENCE: 5 ctctctctct ctctcta 17

<210> SEQ ID NO 6
<211> LENGTH: 17
<212> TYPE: DNA
<213> ORGANISM: Artificial Sequence
<220> FEATURE:
<223> OTHER INFORMATION: A synthetic ISSR PRIMER UBC 818

<400> SEQUENCE: 6 cacacacaca cacacag 17

<210> SEQ ID NO 7
<211> LENGTH: 17
<212> TYPE: DNA
<213> ORGANISM: Artificial Sequence
<220> FEATURE:
<223> OTHER INFORMATION: A synthetic ISSR PRIMER UBC 823

<400> SEQUENCE: 7 tctctctctc tctctcc 17

<210> SEQ ID NO 8
<211> LENGTH: 17
<212> TYPE: DNA
<213> ORGANISM: Artificial Sequence
<220> FEATURE:
<223> OTHER INFORMATION: A synthetic ISSR PRIMER UBC 825

<400> SEQUENCE: 8 acacacacac acacact 17

<210> SEQ ID NO 9
<211> LENGTH: 17
<212> TYPE: DNA
<213> ORGANISM: Artificial Sequence
<220> FEATURE:
<223> OTHER INFORMATION: A synthetic ISSR PRIMER UBC 826

<400> SEQUENCE: 9 acacacacac acacacc 17

<210> SEQ ID NO 10
<211> LENGTH: 17
<212> TYPE: DNA
<213> ORGANISM: Artificial Sequence
<220> FEATURE:
<223> OTHER INFORMATION: A synthetic ISSR PRIMER UBC 828

<400> SEQUENCE: 10 tgtgtgtgtg tgtgtga 17

We claim:

1. A new and distinct variety of a diploid plant named ‘CIMAP-KHUSINOLIKA’ of Vetiver as illustrated and described herein.

* * * * *

DNA Fingerprints of the Clone "CIMAP-KHUSINOL KHUS"

Lane: M (DNA marker), 1-10 (ISSR Marker)
M. Medium range DNA Ruler (GeNei)
1 : UBC807-AGAGAGAGAGAGAGAGT
2 : UBC810-GAGAGAGAGAGAGAGAT
3 : UBC811-GAGAGAGAGAGAGAGAC
4 : UBC812-GAGAGAGAGAGAGAGAA
5 : UBC814-CTCTCTCTCTCTCTCTA
6 : UBC818-CACACACACACACACAG
7 : UBC823-TCTCTCTCTCTCTCTCC
8 : UBC825-ACACACACACACACACT
9 : UBC826-ACACACACACACACACC
10 UBC828-TGTGTGTGTGTGTGTGA